United States Patent
Clifton et al.

(10) Patent No.: US 12,303,313 B2
(45) Date of Patent: May 20, 2025

(54) METHOD OF AND SYSTEM FOR CALCIUM SCORING OF CORONARY ARTERIES

(71) Applicant: Artrya Limited, Perth (AU)

(72) Inventors: Casey Jack Clifton, Subiaco (AU); Jack Rex Joyner, Floreat (AU); Julien Charles Flack, Swanbourne (AU); Girish Dwivedi, Dalkeith (AU); Abdul Rahman Ihdayhid, Ardross (AU)

(73) Assignee: Artrya Limited, Perth (AU)

( * ) Notice: Subject to any disclaimer, the term of this patent is extended or adjusted under 35 U.S.C. 154(b) by 368 days.

(21) Appl. No.: 17/802,890

(22) PCT Filed: Feb. 26, 2021

(86) PCT No.: PCT/AU2021/050168
§ 371 (c)(1),
(2) Date: Aug. 26, 2022

(87) PCT Pub. No.: WO2021/168517
PCT Pub. Date: Sep. 2, 2021

(65) Prior Publication Data
US 2023/0117134 A1 Apr. 20, 2023

(30) Foreign Application Priority Data

Feb. 28, 2020 (AU) .............................. 2020900593
Jun. 22, 2020 (AU) .............................. 2020902072
Jul. 10, 2020 (AU) .............................. 2020902398

(51) Int. Cl.
*A61B 6/00* (2024.01)
*A61B 6/50* (2024.01)
(Continued)

(52) U.S. Cl.
CPC .............. *A61B 6/504* (2013.01); *A61B 6/503* (2013.01); *A61B 6/5217* (2013.01); *G06T 7/10* (2017.01);
(Continued)

(58) Field of Classification Search
CPC . G06T 11/003; G06T 7/10; G06T 7/62; G06T 2207/20084; G06T 2207/10081;
(Continued)

(56) References Cited

U.S. PATENT DOCUMENTS

| 6,233,304 B1 | 5/2001 | Hu et al. |
| 7,409,079 B2 | 8/2008 | Saptharishi et al. |
| (Continued) | | |

FOREIGN PATENT DOCUMENTS

| CN | 109288536 | 2/2019 |
| CN | 109389592 | 2/2019 |
| (Continued) | | |

OTHER PUBLICATIONS

International Preliminary Report on Patentability for PCT Appl. Ser. No. PCT/AU2021/050168 dated May 9, 2022 ( 11 pages).
(Continued)

*Primary Examiner* — Congvan Tran
(74) *Attorney, Agent, or Firm* — Foley & Lardner LLP

(57) ABSTRACT

A method of automatically determining a calcium score for at least one coronary artery is disclosed. The method comprises receiving cardiac non-contrast CT data indicative of a cardiac non-contrast CT scan carried out on a patient, analysing the cardiac non-contrast CT data in a calcified components identifier to detect candidate coronary artery calcified components, and analysing cardiac non-contrast CT data associated with the candidate coronary artery calcified components using a radiomics analyser to determine radiomic characteristics of the candidate coronary artery
(Continued)

calcified components. The method also comprises applying machine learning to the determined radiomic characteristics associated with each candidate coronary artery calcified component to identify any calcifications that are located on a coronary artery, analysing the cardiac non-contrast CT data to identify at least one body component in the cardiac non-contrast CT data not associated with a coronary artery of the patient, and using the identified at least one body component in the cardiac non-contrast CT data to remove or avoid misclassification of calcifications on a coronary artery that are located on the at least one identified body component.

27 Claims, 12 Drawing Sheets

(51) Int. Cl.
  *G06T 7/10* (2017.01)
  *G06T 7/62* (2017.01)
  *G06T 11/00* (2006.01)
(52) U.S. Cl.
  CPC .............. *G06T 7/62* (2017.01); *G06T 11/003* (2013.01); *G06T 2207/10081* (2013.01); *G06T 2207/20081* (2013.01); *G06T 2207/20084* (2013.01); *G06T 2207/30101* (2013.01); *G06T 2207/30204* (2013.01)
(58) Field of Classification Search
  CPC . G06T 2207/20081; G06T 2207/30204; G06T 2207/30101; A61B 6/503; A61B 6/481; A61B 6/504; A61B 6/5217; A61B 6/507; A61B 6/032
  See application file for complete search history.

(56) References Cited

U.S. PATENT DOCUMENTS

| | | | |
|---|---|---|---|
| 7,907,766 | B2 | 3/2011 | Lehel et al. |
| 7,970,196 | B2 | 6/2011 | Arnold et al. |
| 8,970,528 | B2 | 3/2015 | Kojima et al. |
| 10,395,773 | B2 | 8/2019 | Tang |
| 10,542,952 | B2 | 1/2020 | Allmendinger et al. |
| 2008/0159610 | A1* | 7/2008 | Haas ........................ G06T 7/62 |
| | | | 702/19 |
| 2011/0243412 | A1 | 10/2011 | Grass et al. |
| 2018/0276817 | A1* | 9/2018 | Isgum ........................ G06T 7/10 |
| 2019/0138694 | A1* | 5/2019 | Tang ........................ G06T 7/11 |
| 2020/0273167 | A1 | 8/2020 | Wilson et al. |
| 2020/0364853 | A1* | 11/2020 | Tang ..................... G16H 30/40 |

FOREIGN PATENT DOCUMENTS

| | | |
|---|---|---|
| EP | 3 454 301 | 3/2019 |
| EP | 3454301 A1 * | 3/2019 |

OTHER PUBLICATIONS

International Search Report and Written Opinion on PCT Appl. Ser. No. PCT/AU2021/050168 dated Apr. 29, 2021 (11 pages).
Van Assen, Marly, "Quantitative Cardiac Dual Source CT, from Morphology to Function," University of Groningen, Sep. 4, 2019, 346 pages.
Wolterink, et al., "Automatic Coronary Calcium Scoring in Non-Contrast-Enhanced ECG-Triggered Cardiac CT with Ambiguity Detection," IEEE Transactions on Medical Imaging, vol. 34, No. 9, Sep. 2015, pp. 1867-1878.

* cited by examiner

| | Method A | Method B/C |
|---|---|---|
| Training phase | 1055 | 4807 |
| Age – years (SD) | 59.4 (10.8) | 58.4 (11.7) |
| Gender – male (%) | 145 (60.1) | 1108 (56.6) |
| Calcium Score Risk category (%) | 241 | 1958 |
| 0 | 76 (31.5) | 882 (45.0) |
| 1-10 | 26 (10.8) | 255 (13.0) |
| 11-100 | 62 (25.7) | 396 (20.2) |
| 101-400 | 55 (22.8) | 274 (14.0) |
| >400 | 22 (9.1) | 151 (7.7) |

Fig. 7

| CAC\CAC_ML | 0 | 1-10 | 11-100 | 101-400 | >400 | Total | Diagnostic Accuracy (%) |
|---|---|---|---|---|---|---|---|
| 0 | 880 | 5 | 0 | 0 | 0 | 885 | 99.44 |
| 1-10 | 21 | 233 | 11 | 0 | 0 | 265 | 87.92 |
| 11-100 | 4 | 5 | 375 | 267 | 2 | 271 | 96.15 |
| 101-400 | 0 | 0 | 2 | 267 | 2 | 271 | 98.52 |
| >400 | 0 | 0 | 1 | 4 | 142 | 147 | 96.60 |
| Total | 905 | 243 | 389 | 277 | 144 | 1958 | 96.88 |

METHOD OF AND SYSTEM FOR CALCIUM SCORING OF CORONARY ARTERIES

CROSS-REFERENCE TO RELATED APPLICATION

This application is a U.S. National Phase Application of the PCT Application No. PCT/AU2021/050168, filed on Feb. 26, 2021, which is based upon Australian Application No. 2020902398, filed on Jul. 10, 2020, Australian Application No. 2020902072, filed Jun. 22, 2020, an Australian Application No. 2020900593, filed Feb. 28, 2020, the entire contents of each of which are incorporated herein by their reference.

FIELD OF THE INVENTION

The present invention relates to a method of and system for calcium scoring of coronary arteries.

BACKGROUND OF THE INVENTION

Coronary Artery Calcium (CAC) scores are an important indicator of Coronary Artery Disease (CAD) and are commonly calculated using Agatston's method of density weighted area calculation. In current clinical practice, the calculation of CAC scores is a semi-autonomous process that uses software to detect potential areas of calcification, but requires a trained expert to delineate between artery calcification, other vessel calcification, such as aortic calcification, and other calcium containing features such as ribs or spine. This manual process is time consuming and prone to human error.

Known partially automatic calcium scoring techniques typically require registration of a contrast computed tomography (CT) scan with a known feature mask, or require one or more "atlas" images indicative of expected locations of body features to be able to spatially locate the position of the coronary arteries in CT scans.

Methods of detecting coronary calcifications using only non-contrast CT scans are known, but these methods are not able to automatically identify and label individual coronary arteries and significant manual intervention is required.

U.S. Pat. No. 7,907,766 describes a method of automatically generating a calcium score but requires manual intervention to position, rotate and modify a reticle tool on CT images of the patient's heart. The reticle is then used as a reference to identify the locations of coronary features.

U.S. Pat. No. 8,867,822 describes a method of generating a coronary artery calcium score. This method is similar to the method in U.S. Pat. No. 7,907,766, in that although the method does not require manual addition of a reticle to spatially identify the location of coronary features in a scan, it requires addition of a model of the heart and a manual process of aligning the heart model with a CT scan, then using the alignment model to locate the position of the coronary arteries.

Commercial vendors of CT scanners typically provide software to assist radiographers to identify, delineate and label calcifications on CT scans. However, since each company has different CT scanning technology and associated software for calcium scoring, inconsistencies between results from different vendors exist. In addition, the reliance on human operators to identify and delineate the extent of calcified plaques may lead to additional inconsistency through human error.

SUMMARY OF THE INVENTION

In accordance with a first aspect of the present invention, there is provided a method of automatically determining a calcium score for at least one coronary artery, the method comprising:
  receiving cardiac non-contrast CT data indicative of a cardiac non-contrast CT scan carried out on a patient;
  analysing the cardiac non-contrast CT data in a calcified components identifier to detect candidate coronary artery calcified components;
  analysing cardiac non-contrast CT data associated with the candidate coronary artery calcified components using a radiomics analyser to determine radiomic characteristics of the candidate coronary artery calcified components;
  applying machine learning to the determined radiomic characteristics associated with each candidate coronary artery calcified component to identify any calcifications that are located on a coronary artery;
  analysing the cardiac non-contrast CT data to identify at least one body component in the cardiac non-contrast CT data not associated with a coronary artery of the patient; and
  using the identified at least one body component in the cardiac non-contrast CT data to remove or avoid misclassification of calcifications on a coronary artery that are located on the at least one identified body component.

In an embodiment, the method comprises using machine learning to analyse the cardiac non-contrast CT data to identify at least one body component in the cardiac non-contrast CT data not associated with a coronary artery of the patient. The machine learning step may use a convolutional neural network. The convolutional neural network may be a Unet or Vnet neural network.

In an embodiment, the method comprises applying a connected component analysis to voxels of the cardiac non-contrast CT data to identify neighbouring voxels that belong to the same body component.

In an embodiment, the method comprises:
  analysing the cardiac non-contrast CT data to identify aortic components in the cardiac non-contrast CT data associated with an aorta of the patient; and
  using the identified aortic components of the cardiac non-contrast CT data to remove or avoid misclassification of calcifications on a coronary artery that are located on the aortic components.

In an embodiment, the method comprises analysing the cardiac non-contrast CT data to identify ascending and descending portions of the aorta.

In an embodiment, the method comprises using machine learning to predict whether each voxel of the cardiac non-contrast CT data is part of the ascending or descending aorta and produce candidate aorta voxels.

In an embodiment, the method comprises applying a connected component analysis to the candidate aorta voxels to identify neighbouring voxels that belong to the same aortic component. The connected component analysis may use 8, 16 or 26 connectivity.

In an embodiment, the step of analysing the cardiac non-contrast CT data to identify aortic components of the cardiac non-contrast CT data associated with an aorta of the patient comprises analysing the identified aortic components using size, shape and position of the identified aortic components.

In an embodiment, the step of analysing the cardiac non-contrast CT data to identify aortic components in the cardiac non-contrast CT data associated with an aorta of the patient comprises progressively processing single slices of the cardiac non-contrast CT data, and assembling the results of a plurality of individual slices into a volumetric segmentation.

In an embodiment, the method comprises the step of analysing the cardiac non-contrast CT data to identify aortic components in the cardiac non-contrast CT data associated with an aorta of the patient comprises processing volumetric inputs or cross-hair type orthogonal inputs.

In an embodiment, the method comprises the step of analysing the cardiac non-contrast CT data to identify aortic components in the cardiac non-contrast CT data associated with an aorta of the patient uses a convolutional neural network.

In an embodiment, the method comprises:
analysing the cardiac non-contrast CT data to identify a cardiac region of interest (ROI) around a heart in the cardiac non-contrast CT data; and
using the identified cardiac ROI to remove or avoid misclassification of calcifications on a coronary artery that are located outside the cardiac ROI.

In an embodiment, the method comprises using machine learning to analyse the cardiac non-contrast CT data to identify the cardiac ROI.

In an embodiment, the method comprises using machine learning to predict whether each voxel of the cardiac non-contrast CT data is part of the cardiac ROI.

In an embodiment, the step of analysing the cardiac non-contrast CT data to detect candidate coronary artery calcified components comprises applying a radiodensity test to voxels of the cardiac non-contrast CT data, and passing only voxels that have a radiodensity above a defined threshold. The radiodensity test may be a Hounsfield Unit test, such as a 130 Hounsfield Unit test.

In an embodiment, the method comprises applying a connected component analysis to voxels passed by the radiodensity test to identify neighbouring voxels that belong to the same calcified component.

In an embodiment, the determined radiomic characteristics include position, shape, size and/or density.

In an embodiment, the step of applying machine learning to the determined radiomic characteristics associated with each candidate coronary artery calcified component comprises using at least one classifier.

In an embodiment, the method comprises using a first classifier to classify each candidate coronary artery calcified component as located on a coronary artery or not located on a coronary artery, and a second classifier to identify each coronary artery.

In an embodiment, the at least one classifier includes a random forest and/or a K-nearest-neighbour classifier.

In an embodiment, the outputs of the classifiers are combined according to a weighted voting mechanism.

In an embodiment, the step of applying machine learning to the determined radiomic characteristics associated with each candidate coronary artery calcified component comprises using at least one neural network.

In an embodiment, the method comprises analysing the cardiac non-contrast CT data indicative of the candidate coronary artery calcified components to determine image patch data associated with a region of the cardiac non-contrast CT data around each candidate coronary artery calcified component, and applying machine learning to the determined image patch data to identify any calcifications that are located on a coronary artery.

In an embodiment, the step of applying machine learning to the determined image patch data to identify any calcifications that are located on a coronary artery comprises using a convolutional neural network.

In an embodiment, the method comprises using a hybrid neural network to combine the output of the step of applying machine learning to the determined image patch data to identify any calcifications that are located on a coronary artery using a convolutional neural network, and the output of the step of determining radiomic characteristics associated with each candidate coronary artery calcified component using at least one neural network.

In an embodiment, the method comprises directly applying machine learning to the cardiac non-contrast CT data indicative of the candidate coronary artery calcified components to identify any calcifications that are located on a coronary artery.

In an embodiment, the method comprises using outputs of the directly applied machine learning and outputs of the radiomic machine learning to identify any calcifications that are located on a coronary artery.

In an embodiment, the method comprises combining the outputs of the directly applied machine learning and the outputs of the radiomic machine learning using a voting mechanism.

In an embodiment, the method comprises:
analysing the cardiac non-contrast CT data to identify a mitral valve in the cardiac non-contrast CT data; and
using the identified mitral valve to remove or avoid misclassification of calcifications.

In an embodiment, the method comprises:
analysing the cardiac non-contrast CT data to identify a heart in the cardiac non-contrast CT data; and
using the identified heart to remove or avoid misclassification of calcifications on a coronary artery that are located outside the heart.

In an embodiment, the method comprises:
analysing the cardiac non-contrast CT data to identify coronary arteries by identifying the ostia and tracking from the ostia across the coronary arteries using machine learning or sematic segmentation.

In an embodiment, the method comprises adding calibration markers manually to the cardiac non-contrast CT data and using the added markers to provide the machine learning with positional information.

In accordance with a second aspect of the present invention, there is provided a system for automatically determining a calcium score for at least one coronary artery, the system comprising:
a calcified components identifier for analysing received cardiac non-contrast CT data indicative of a cardiac non-contrast CT scan carried out on a patient to detect candidate coronary artery calcified components;
a radiomics analyser for analysing cardiac non-contrast CT data associated with the candidate coronary artery calcified components to determine radiomic characteristics of the candidate coronary artery calcified components;
a radiomic machine learning component arranged to apply machine learning to the determined radiomic characteristics associated with each candidate coronary artery calcified component to identify any calcifications that are located on a coronary artery;
a body component identifier arranged to analyse the cardiac non-contrast CT data to identify at least one body component in the cardiac non-contrast CT data not associated with a coronary artery of the patient; and a misclassification remover that uses the identified at least one body component in the cardiac non-contrast CT data to remove or avoid misclassification of calcifications on a coronary artery that are located on the at least one identified body component.

In accordance with a third aspect of the present invention, there is provided a method of automatically determining a calcium score for at least one coronary component, the method comprising:

receiving cardiac non-contrast CT data indicative of a cardiac non-contrast CT scan carried out on a patient;

analysing the cardiac non-contrast CT data in a calcified components identifier to detect at least one candidate coronary calcified component associated with at least one target coronary anatomical structure;

analysing cardiac non-contrast CT data associated with the at least one candidate coronary calcified component using a radiomics analyser to determine radiomic characteristics of the at least one candidate coronary calcified component;

applying machine learning to the determined radiomic characteristics associated with each candidate coronary calcified component to identify any calcifications that are located on the at least one target coronary anatomical structure;

analysing the cardiac non-contrast CT data to identify at least one body component in the cardiac non-contrast CT data not associated with the at least one target coronary anatomical structure; and using the identified at least one body component in the cardiac non-contrast CT data to remove or avoid misclassification of calcifications on the at least one coronary target anatomical structure that are located on the at least one identified body component.

In accordance with a fourth aspect of the present invention, there is provided a system for automatically determining a calcium score for at least one coronary component, the system comprising:

a calcified components identifier for analysing received cardiac non-contrast CT data indicative of a cardiac non-contrast CT scan carried out on a patient to detect at least one candidate coronary calcified component associated with at least one target coronary anatomical structure;

a radiomics analyser for analysing cardiac non-contrast CT data associated with the at least one candidate coronary calcified component to determine radiomic characteristics of the at least one candidate coronary calcified component;

a radiomic machine learning component arranged to apply machine learning to the determined radiomic characteristics associated with each candidate coronary calcified component to identify any calcifications that are located on the at least one target coronary anatomical structure;

a body component identifier arranged to analyse the cardiac non-contrast CT data to identify at least one body component in the cardiac non-contrast CT data not associated with the at least one target coronary anatomical structure; and a misclassification remover that uses the identified at least one body component in the cardiac non-contrast CT data to remove or avoid misclassification of calcifications on the at least one coronary target anatomical structure that are located on the at least one identified body component.

BRIEF DESCRIPTION OF THE DRAWINGS

The present invention will now be described, by way of example only, with reference to the accompanying drawings, in which:

FIG. 7 is a test patient demographic table associated with example implementations of a coronary artery calcium scoring system and method;

DESCRIPTION OF AN EMBODIMENT OF THE INVENTION

The present disclosure relates to an automated method for detection of calcifications on coronary arteries using cardiac computed tomography (CT) scans. The method and system disclosed are able to detect and characterise calcifications in coronary arteries of a patient from non-contrast CT scans, and label coronary arteries, without the need to inject a contrast agent into the patient.

The current method and system circumvents the need for a reticle or other spatial alignment mechanism, such as a heart model, to locate the coronary arteries and subsequently determine whether calcifications are present on the coronary arteries.

The disclosed method includes a sequence of steps configured using machine learning to detect and identify coronary calcifications.

The system and method described uses machine learning techniques and radiomics, which enables enough information to be extracted from a non-contrast CT scan to correctly identify coronary calcifications and the artery they pertain to, without the need for contrast enhancement of the arteries or manual guidance. The method uses machine learning to determine the most likely classification of every voxel in the CT scan, and machine learning to identify non-coronary artery features, which can then be used to remove or avoid misclassifications of components as calcified coronary artery components.

In the present example system and method, two groups of machine learning classifiers are used to classify voxels of candidate calcifications, and the non-coronary artery features are identified using semantic segmentation of the ascending and descending aorta and identification of a cardiac region of interest (ROI).

Figure 1:
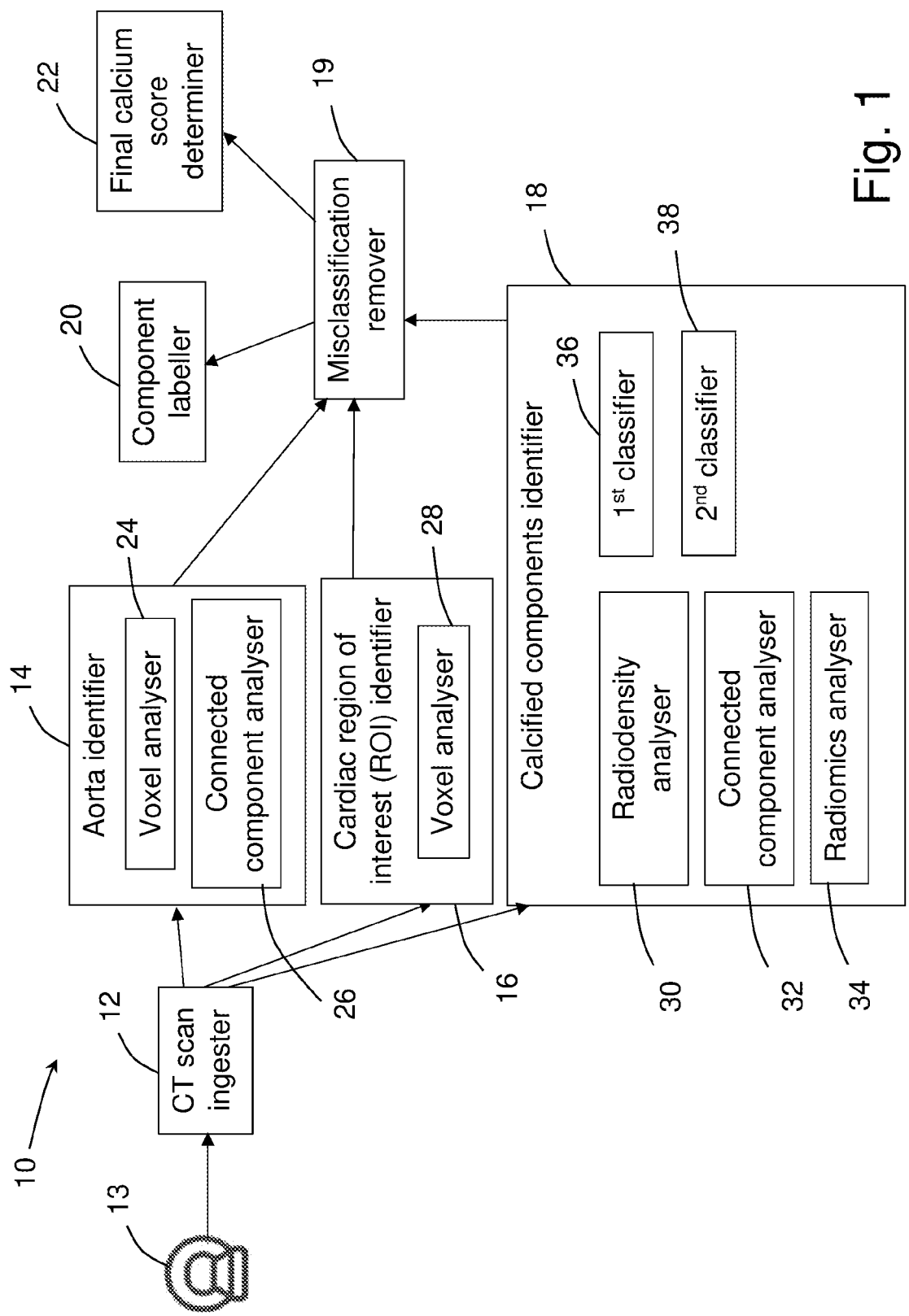
FIG. 1 is a schematic block diagram of a system for calcium scoring according to an embodiment of the present invention.

Referring to FIG. 1 of the drawings, an example system 10 for calcium scoring of coronary arteries is shown. The system 10 includes a CT scan ingester 12 arranged to receive cardiac non-contrast CT data from a CT scanning device 13, an aorta identifier 14 for identifying ascending and descending aorta components in the cardiac non-contrast CT data, a cardiac region of interest (ROI) identifier 16 for identifying a cardiac ROI in the cardiac non-contrast CT data, a calcified components identifier 18 for identifying calcified components in the cardiac non-contrast CT data, a misclassification remover 19 that uses the information from the aorta identifier 14 and the cardiac ROI identifier 16 to remove calcified volumes from consideration, a component labeler 20 and a final calcium score determiner 22.

In this example, the aorta identifier 14 includes a voxel analyser 24 arranged to predict using machine learning whether each voxel in received patient cardiac non-contrast CT data is part of the ascending or descending aorta of the patient, and a connected component analyser 26 arranged to use a connected component technique to identify neighbouring voxels that belong to particular components of the ascending or descending aorta.

The aorta identifier 14 produces a machine learning voxel mask that can be used to remove from consideration calcifications present on the ascending or descending aorta and therefore not on the coronary arteries.

In this example, the cardiac region of interest (ROI) identifier 16 includes a voxel analyser 28 arranged to predict, using machine learning, voxels in received patient cardiac non-contrast CT data that are part of a region of interest around the heart of the patient.

In this example, the calcified components identifier 18 includes a radiodensity analyser 30 arranged to identify candidate voxels associated with calcified components, for example by applying a Hounsfield Unit thresholder to the voxel data so that only voxels with an associated radiodensity above a defined level are passed.

The calcified components identifier 18 also includes a connected component analyser 32 arranged to use a connected component technique to identify neighbouring voxels that belong to the same calcified component, and a radiomics analyser 34 arranged to analyse the identified calcified components to obtain a set of characteristics for each component.

In the field of medicine, radiomics is used to extract information from radiographic medical images. The present inventors have realised that such radiomic features have the potential to be used in a machine learning system to identify and locate coronary artery calcifications. By analysing each candidate calcification component using a radiomics engine, characteristics describing the relative position, shape, size and texture of the components are obtained, and these characteristics are chosen to provide a rich description of the components that can be used by machine learning systems to learn to distinguish bone from coronary arteries as well as the specific artery in which the component is located. Prior to training, radiomic feature selection is performed by a principal component analysis (PCA) and variance thresholding. PCA is used to automatically determine which features provide the most discriminative power for the machine learning system. This approach provides additional benefits over the traditional prior art approach of hand-crafting specific features. A deep learning model may also look at image patches of raw CT data around each component in order to provide greater context.

The calcified components identifier 18 also includes a machine learning component, in this example a first classifier 36 and a second classifier 38, the classifiers trained to output a determination as to whether a candidate calcification is present on a coronary artery, and the particular coronary artery in which the calcification is disposed.

Figure 2:
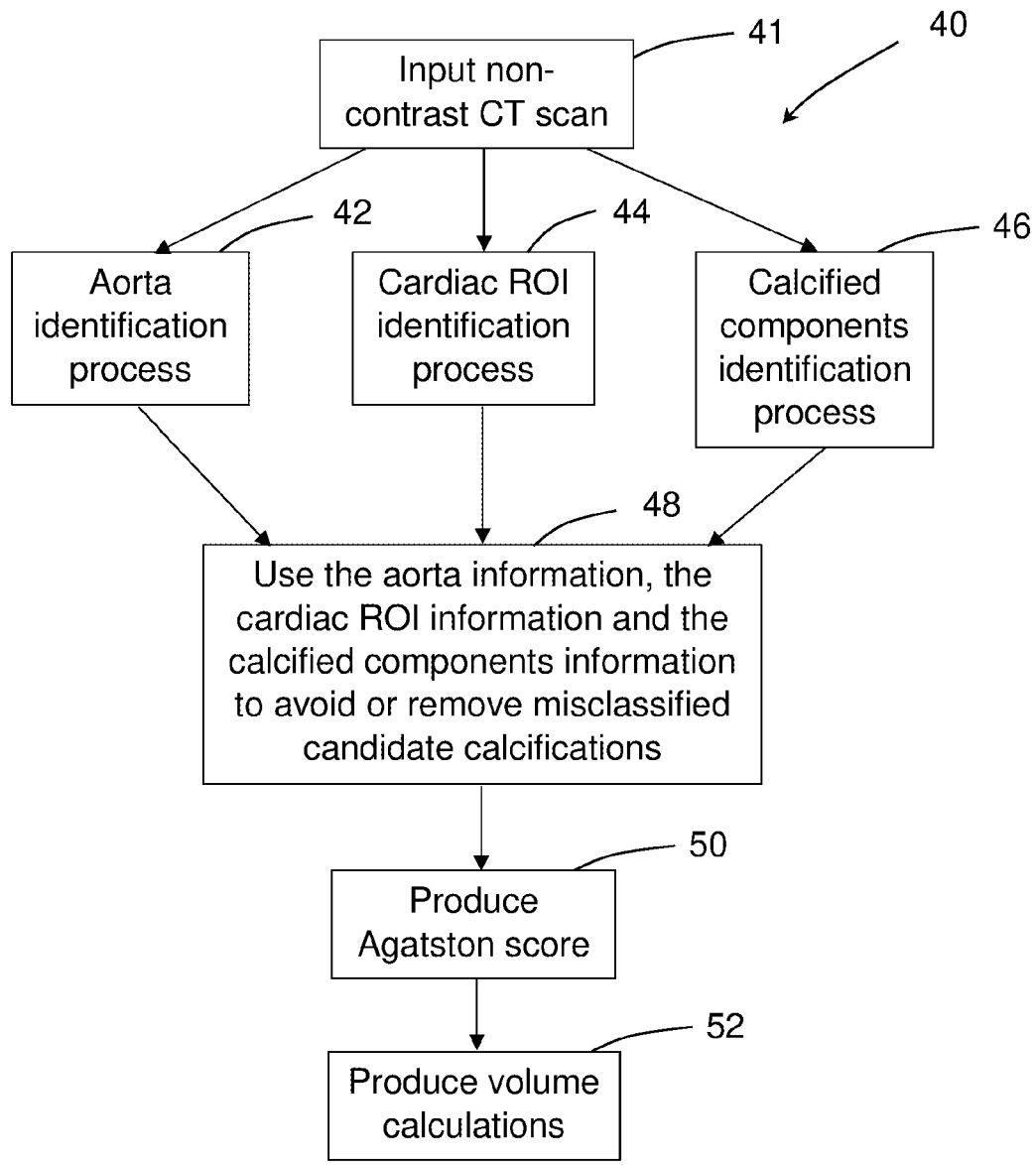
FIG. 2 is a flow diagram illustrating a method of calcium scoring using cardiac non-contrast CT data according to an embodiment of the present invention.

FIG. 2 is a flow diagram 40 illustrating a method of detecting calcifications on coronary arteries using the system 10. According to the present method, cardiac non-contrast CT data is ingested 41 and the scan data is then analysed using an aorta identification process 42, a cardiac region of interest (ROI) identification process 44 and a calcified components identification process 46.

In the examples described, each of the calcified components identification process 42, the aorta identification process 44 and the cardiac region of interest (ROI) identification process 46 uses a machine learning system that is trained using a sufficient number of relevant, known outcome, non-contrast CT scans. In the example described in relation to FIGS. 1 to 6b, the aorta identification process 44 and the cardiac region of interest (ROI) identification process 46 use a convolutional neural network (CNN), and the calcified components identification process 42 uses a plurality of classifiers, in this example 2 classifiers. However, other arrangements are possible. For example, instead of using classifiers for the calcified components identification process 42, a standard neural network may be used. The output of the standard neural network may be combined with other data relevant to coronary artery calcified components identification, such as the output of a convolutional neural network arranged to analyse image patches around candidate calcified components in the cardiac non-contrast CT data.

In this embodiment, the aorta identification process 42 uses machine learning, in this example one or more deep learning models, to perform a semantic segmentation process on the scan data to identify the 3D structures of the ascending and descending aorta. The predicted ascending and descending aorta information is subsequently used as a machine learning mask to remove from consideration candidate calcifications that are present on the ascending or descending aorta and not on a coronary artery.

Figure 3A:
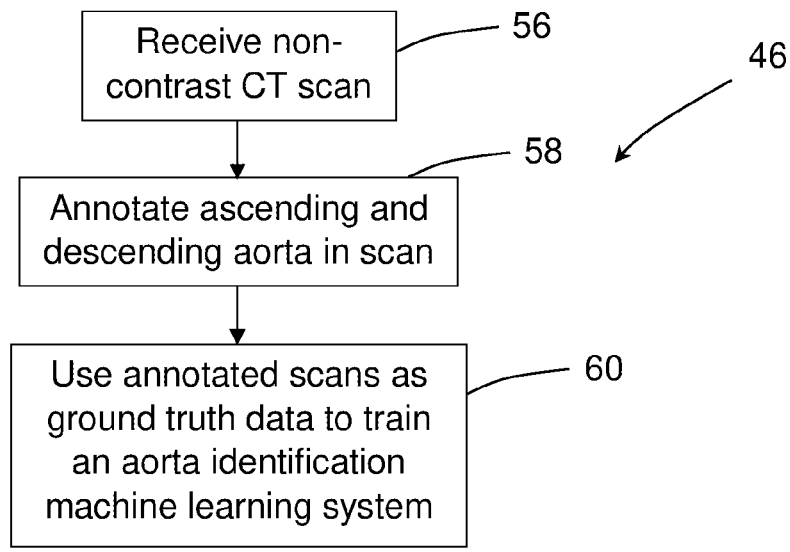
FIG. 3a is a flow diagram illustrating a training process for a machine learning component of an aortic feature identification process referred to in FIG. 2.
Figure 3B:
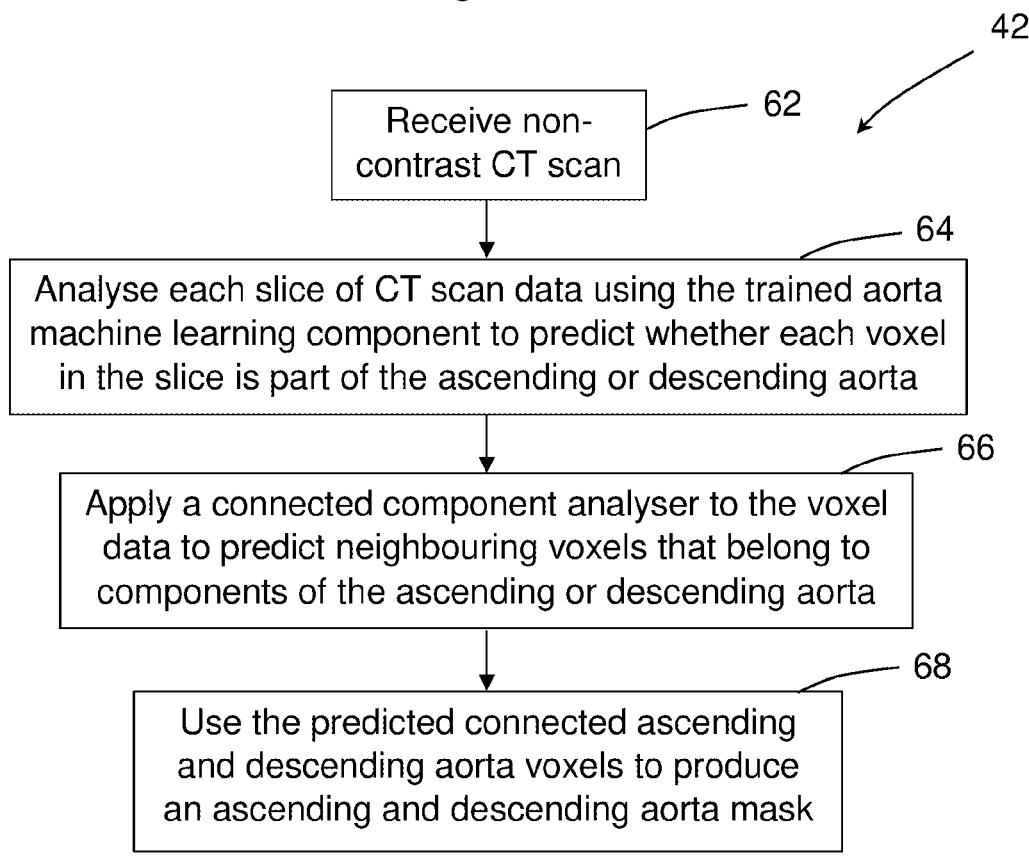
FIG. 3b is a flow diagram illustrating the aortic feature identification process referred to in FIG. 2.

The aorta identification process is shown in more detail in FIGS. 3a and 3b. FIG. 3a illustrates a training process for the machine learning component of the aorta identification process, and FIG. 3b illustrates the aorta identification process during use.

The aorta identification process is arranged to identify the spatial extents of the aorta using semantic segmentation, and uses a deep learning approach to generate for each voxel a probability that the voxel belongs to the aorta. The resultant voxel probability map is then used to determine components in the CT scan that are most likely to correspond to components of the ascending and descending aorta.

Referring to FIG. 3a, in order to train the machine learning component of the aorta identification process 42, non-contrast CT scan data covering the coronary region of a plurality of patients is received 56 and CT scan images of the ascending and descending aorta components are annotated 58 by experts so that a library of ground truth training data is produced. The ground truth aorta training data derived from each scan constitutes a map of voxels identified as being part of the ascending or descending aorta, and the aorta machine learning component is trained 60 using the aorta maps to recognise components of a CT scan that are part of the ascending or descending aorta. However, it will be appreciated that the training process should cover representative samples of the expected patient variation in the input cardiac non-contrast CT data.

In the present method and system, the aorta machine learning component is configured to progressively process single "axial" slices of the CT scan, and assemble the results from a series of individual slices of the CT scan into a volumetric segmentation. However, it will be understood that other implementations are envisaged. For example, the present method and system is not limited to processing multiple individual slices but may also be configured to process volumetric inputs or cross-hair type orthogonal inputs. A cross-hair type volumetric analysis uses an approximation methodology wherein 3 orthogonal slices, each centred on the voxel of interest, are processed to produce an approximation of a full volumetric analysis centred on the voxel of interest.

After the aorta machine learning component has been trained, the aorta identification process 42 illustrated in FIG. 3b can be applied to cardiac non-contrast CT data to produce an ascending/descending aorta mask that can be used to remove misclassifications of candidate calcified components.

Referring to FIG. 3b, received patient cardiac non-contrast CT data is received 62 and analysed 64 using the trained aorta machine learning component to predict whether each voxel in the cardiac non-contrast CT data is part of the ascending or descending aorta, then the voxel data is analysed 66 using a connected component technique to identify neighbouring voxels of the ascending or descending aorta and in turn identify components of the ascending and descending aorta in the cardiac non-contrast CT data.

Those skilled in the art of will appreciate that various suitable machine learning arrangements are envisaged for implementing aorta feature recognition, for example a wide variety of convolutional neural networks (CNN) can be effectively employed for semantic segmentation. In medical applications, the Unet and Vnet type CNN architectures are commonly used.

In the present example, the predicted voxel data is processed using a connected component technique to identify voxels that correspond to adjacent connected components of the ascending or descending aorta and to detect outliers by identifying neighbouring voxels using 8, 16 or 26 connectivity, although it will be understood that other techniques are envisaged.

Each aortic component identified using the connected component technique is analysed according to its size, shape and position, and the most likely candidate for each part of the aorta is chosen. Outlier detection rejects any identified connected component that is too small or in a position that is inconsistent with the ascending and descending aorta. The region, size and position constraints for outlier detection is dependent on the characteristics of the CT scan, including spatial resolution and position of the scan relative to the patient.

In this embodiment, the cardiac ROI process 44 uses machine learning, in this example one or more deep learning models, to identify a region of interest (ROI) adjacent the heart. The predicted cardiac ROI information is used as a mask to remove outlier candidate calcifications that are present outside the cardiac ROI and therefore not present on a coronary artery. A deep learning approach is used to predict the probability that each voxel belongs to the cardiac ROI. It will be understood that the cardiac ROI indicates an area of the scan in which coronary arteries are located and therefore coronary artery calcification may occur, and by removing areas outside the cardiac ROI from consideration, features such as the lungs, ribs and spine are ignored. This improves both the speed and accuracy of classifying potential calcifications.

By removing cardiac non-contrast CT data that is associated with regions outside the heart, the likelihood of false positive classifications is reduced, and unnecessary radiomic analysis of calcifications outside the heart, such as of the spine and ribs, can be avoided. As ROI segmentation is a relatively fast method of identifying calcifications outside the heart as non-coronary artery calcifications, the total time to produce a final calcium score result is reduced.

Figure 4A:
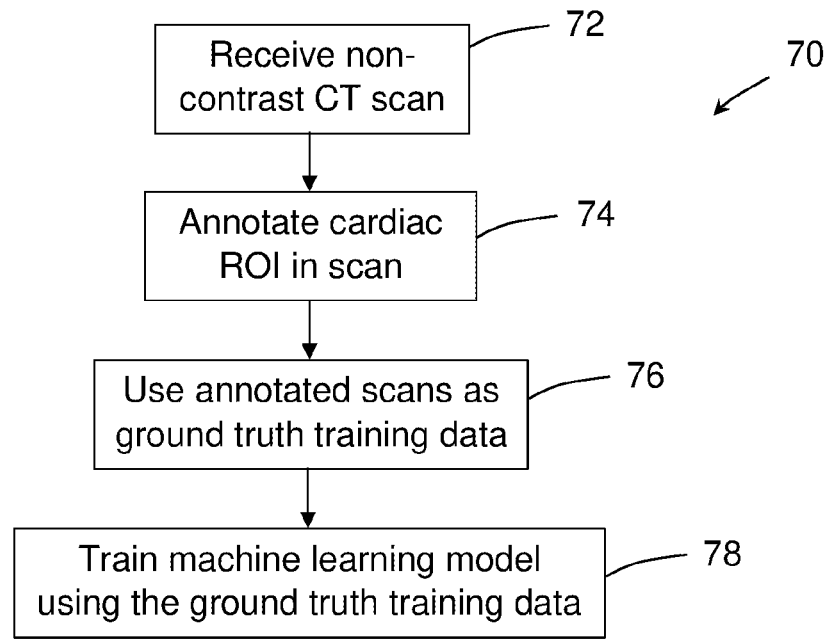
FIG. 4a is a flow diagram illustrating a training process for a machine learning component of a cardiac ROI identification process referred to in FIG. 2.
Figure 4B:
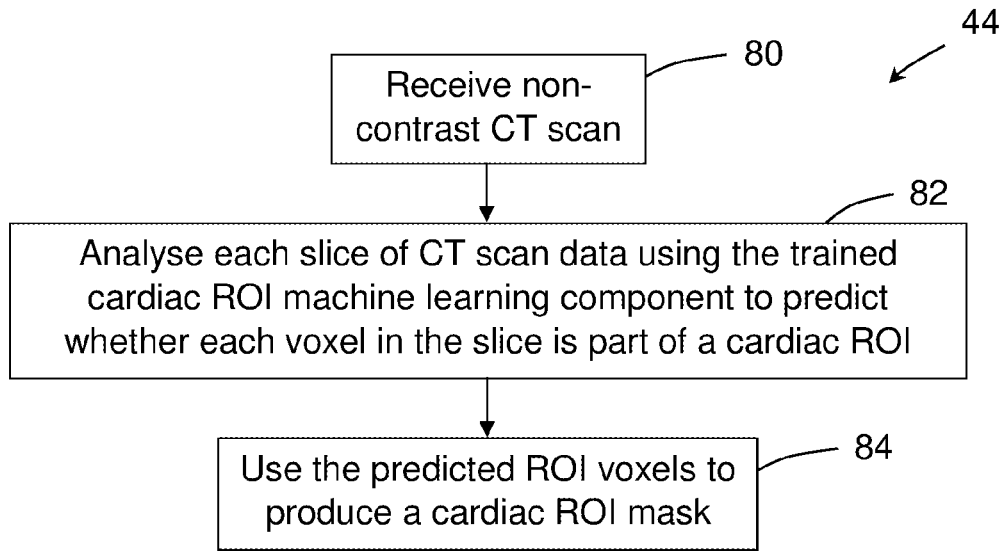
FIG. 4b is a flow diagram illustrating the cardiac region of interest (ROI) process referred to in FIG. 2.

The cardiac ROI process 44 is shown in more detail in FIGS. 4a and 4b. FIG. 4a illustrates a training process 70 for the machine learning component of the cardiac ROI process 44, and FIG. 4b illustrates the cardiac ROI process 44 during use.

Referring to FIG. 4a, in order to train the machine learning component of the cardiac ROI identification process, non-contrast cardiac non-contrast CT data covering the coronary region of a plurality of patients is received 72 and the CT scan images of the ROI around the heart are annotated 74 by experts so that a library of ground truth training data is produced. The ground truth cardiac ROI training data derived from each scan constitutes a map of voxels identified as being part of the cardiac ROI, and the cardiac ROI machine learning component is trained 76, 78 using the cardiac ROI maps to recognise components of a CT scan that are part of the cardiac ROI. Those skilled in the art of deep learning will appreciate that the maps should cover a representative sample of the expected patient variation in the input cardiac non-contrast CT data.

In the present method and system, the cardiac ROI identification process is configured to progressively process single "axial" slices of the CT scan, and assemble the results from a series of individual slices of the CT scan into a volumetric segmentation. However, it will be understood that other implementations are envisaged. For example, the present method and system is not limited to using single slice but may also be configured process volumetric inputs or cross-hair type orthogonal inputs.

After the cardiac ROI machine learning component has been trained, the cardiac ROI identification process 44 illustrated in FIG. 4b can be applied to cardiac non-contrast CT data.

Referring to FIG. 4b, during use patient cardiac non-contrast CT data is received 80 and analysed 82 using the trained cardiac ROI machine learning component to predict whether each voxel in the cardiac non-contrast CT data is part of the cardiac ROI and produce 84 a cardiac ROI mask that can be used to remove outlier candidate calcifications that are present outside the cardiac ROI.

Figure 5:
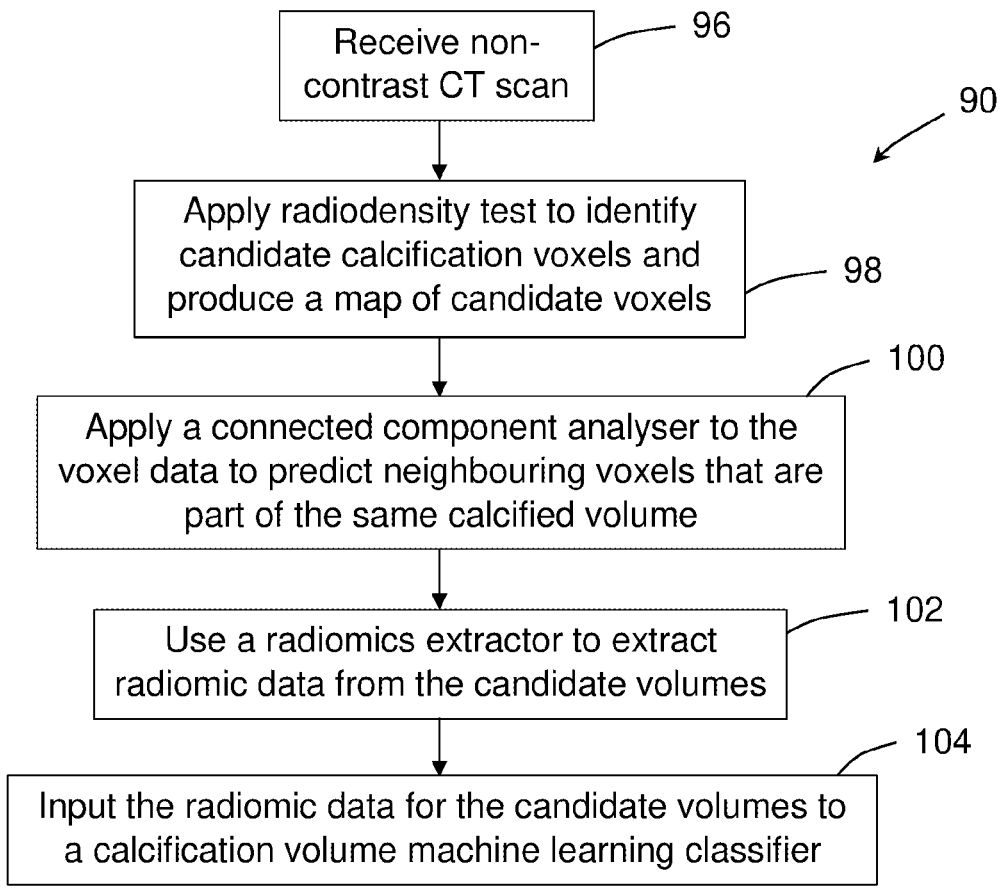
FIG. 5 is a flow diagram illustrating a process for identification of candidate calcified components and obtaining a set of (radiomic) characteristics for the candidate components.
Figure 6A:
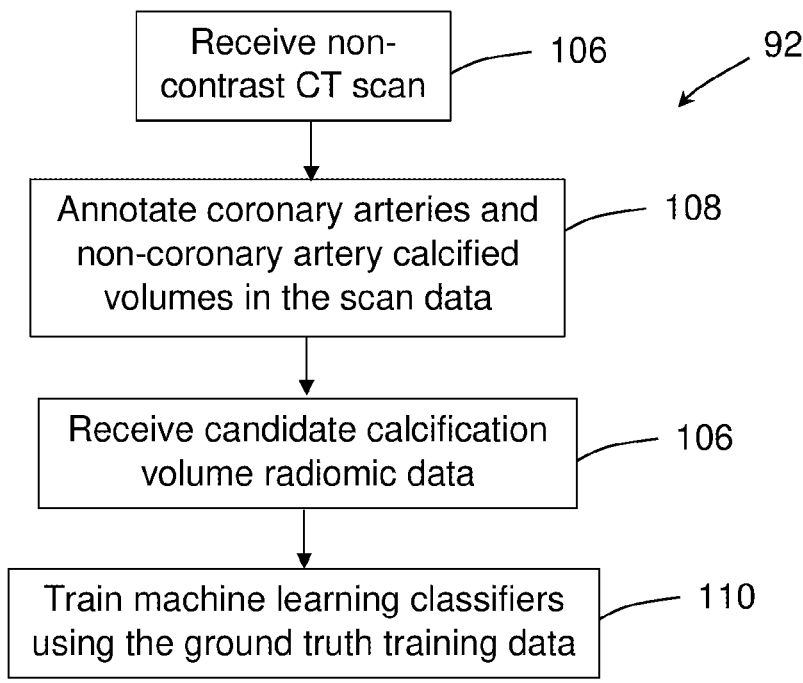
FIG. 6a is a flow diagram illustrating a training process for a machine learning component of a process for classifying candidate calcified components.
Figure 6B:
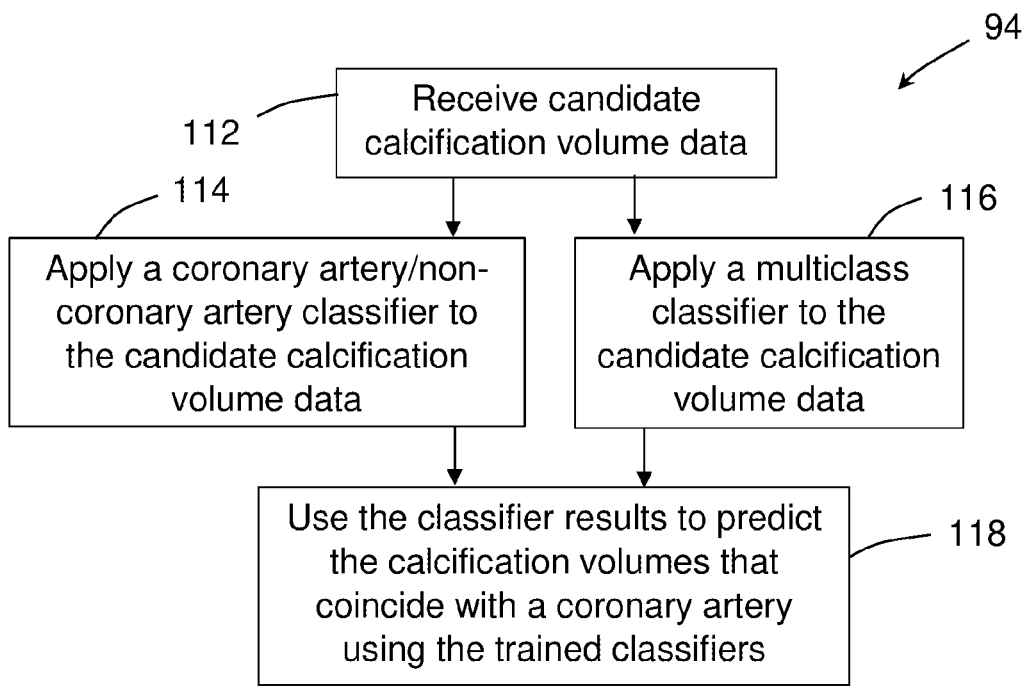
FIG. 6b is a flow diagram illustrating the process for classifying candidate calcified components.

The calcified components identification process 46 is shown in more detail in FIGS. 5, 6a and 6b. FIG. 5 illustrates a process 90 for obtaining candidate calcification radiomic data for input into a calcification machine learning system. FIG. 6a illustrates a training process 92 for the machine learning component of a radiomic characteristics analysis process 94, and FIG. 6b illustrates the radiomic characteristic analysis process 94 during use.

In this example, the radiomics characteristics describe the relative position, shape, size and/or density of each component, although it will be understood that any radiomic characteristic associated with an identified calcified volume and obtainable from radiographic medical imaging data is envisaged.

In addition to the radiomic characteristic information, other information that is capable of assisting identification and classification of coronary artery calcifications may be used. For example, raw CT scan image patch information indicative of a region around each candidate calcification may be input to the classifiers or to an additional machine learning system. Such image patches are capable of providing useful contextual information for each calcification.

In an example implementation, the component characteristics are input into a plurality of trained machine learning classifiers that have been trained to detect the locations of the components based on the characteristics. Alternatively, the component characteristics are used as inputs, for example with raw image data, to a trained deep learning model which predicts the location of the components based on the characteristics.

Referring to FIG. 5, the process 90 for obtaining candidate calcification radiomic data comprises receiving 96 non-contrast cardiac non-contrast CT data, applying 98 a radiodensity test, such as a 130 Hounsfield Unit threshold test, to identify candidate calcification voxels and produce a map of candidate voxels, applying 100 a connected component analysis process to the candidate voxel map so as to predict neighbouring voxels that are part of the same calcified volume, using 102 a radiomics analyser 34 to extract radiomic data from the candidate volumes and produce a set of radiomic characteristics for each candidate volume, and inputting 104 the radiomic data to a calcification volume machine learning system, in this example that comprises one or more machine learning classifiers.

Referring to FIG. 6a, in order to train the machine learning component of the radiomics characteristics analysis process, non-contrast CT scan image data covering the coronary region of a plurality of patients is received 106, and the CT scan images are labelled by an expert to mark the coronary arteries and any non-coronary artery components, such as for example related to bone. Candidate radiomic data associated with the CT scan images are also received. The annotated CT scans and associated candidate radiomic data constitutes a library of ground truth training data that is used to train 2 machine learning classifiers, as indicated at step 110. Those skilled in the art of deep learning will appreciate that the masks should cover a representative sample of the expected patient variation in the input cardiac non-contrast CT data.

After the classifiers have been trained, the radiomics analysis process 94 illustrated in FIG. 6b can be applied to the radiomics data associated with the candidate volumes produced by the process 90 shown in FIG. 5. According to the method, candidate calcification volume (radiomic) data is received 112 and input 114, 116 to a first classifier arranged to classify each volume as belonging to a coronary artery or not, and a second classifier arranged to determine the specific coronary artery on which a calcified volume is considered to be present. The classifier results are then used to predict 118 the calcifications that belong to a coronary artery and label the coronary arteries.

A range of models are envisaged for the classifiers, including random forest and K-nearest-neighbour classifiers. The classifiers may be combined according to a weighted voting mechanism that relates to the training performance of the individual models. Those skilled in the art will appreciate that ensemble vote classification mechanisms including hard and soft voting are appropriate implementations of the weighted voting mechanism.

In this embodiment, each classifier's prediction is combined through a voting mechanism to produce a final predicted probability for each candidate component, although other arrangements are envisaged. For example, labelling calcified plaques may involve a deep learning architecture that learns to delineate between coronary artery calcifications on the left main (LM), Left anterior descending (LAD), right coronary artery (RCA), left circumflex (LCX), and that also learns to detect false positives that are due to noise in the scan, the spine, ribs and aorta.

In an alternative arrangement, the final training process involves generation of expert annotations by trained professionals, who label each coronary artery as well as components that are either bone or noise. Image patches and the characteristics generated by the process in FIG. 5 are input to the deep learning model. The model trains by backpropagation to optimise classification of each component.

As indicated at step 48 of the flow diagram in FIG. 2, the predicted candidate calcifications produced by the trained machine learning classifiers are cross-checked against the predicted ascending and descending aorta information and the predicted cardiac ROI information and any candidate calcifications that are considered to relate to noise, or to be present on the ascending or descending aorta, or located outside the cardiac ROI, are removed. The Agatston score and calcium volumes are then calculated on the remaining candidate components, as indicated at steps 50 and 52, and the coronary arteries labelled, as indicated at step 53.

In the present embodiment, the misclassification removal step, wherein candidate calcifications are cross-checked against the predicted ascending and descending aorta information and the predicted cardiac ROI information, is carried out after all candidate calcified volumes have been analysed by the calcified components identifier and radiomic characteristics produced. However, it will be understood that other arrangements are possible. For example, the misclassification removal step may be carried out after candidate volumes have been identified by the radiodensity analyser 30 and the connected component analyser 32, but before analysis by the radiomics extractor; or for example the misclassification removal step using the cardiac ROI information is carried out on raw CT image data. In this way, unnecessary radiomic processing of calcified volumes that are located on the ascending or descending aorta or outside a region around the heart is avoided.

It will be appreciated that the present method reduces risk to a patient by removing need for contrast enhancement, reduces cost to a patient by removing need for second CT scan, and reduces cost to a clinic by reducing labour required to produce calcium score.

In a variation, the aorta identifier 14 may also segment the mitral valve. Similar to the process described in FIG. 3b, this variation relies on ground-truth annotations of the mitral valve in order to train a deep learning model to output a prediction for each voxel as to the likelihood that the voxel is associated with the mitral valve. A Hounsfield Unit threshold may then be applied to the valve's segmentation mask in order to calculate calcification.

A heart segmentation process may also be carried out in order to improve false positive detection and thereby prevent misclassification of ribs or spine as coronary arteries. This segmentation may take the form of a further deep learning model, such as a CNN, trained for detection of large aspects of the CT scan that indicate the location of the heart, including the ribs, spine, lungs and heart itself.

Aorta segmentation may also be used to create relative position features for each candidate calcified component. An additional use of the aorta segmentation involves performing the process prior to, rather than simultaneously with, the calcified components identification process shown in FIGS. 5 and 6b. With information regarding the spatial extent of the ascending and descending aorta, additional characteristics such as the location of a calcified component relative to each aorta structure create a richer description, and therefore more accurate classification, of the components.

Classification of voxels using CNN machine learning architecture may also be carried out using raw or processed image data to augment radiomic feature-based classification of components. In a variation of classification by pre-calculated radiomic characteristics, a deep learning model, such as a CNN, whose only input is the raw image of the component, may perform classification of each component, and the output of this process then provided, with the output of the radiomic characteristic based classification, into a voting mechanism to determine the most probable classification for each component.

A further aspect may include localisation of the coronary arteries prior to the image analysis and feature creation step of FIG. 5. Detection of the arteries in a non-contrast scan may occur by techniques such as artery tracking, which locate the ostia and move step-by-step through the arteries with guidance from a deep learning model such as a CNN, or by semantic segmentation in a way similar to the aorta identification proves described in FIG. 3b. Each component can then be additionally characterised by its proximity to the coronary arteries, creating a richer description that is input to the machine learning classifiers.

Further enhancement of the characteristics used to describe calcified components may come from use of manually inserted calibration markers at the top of scan. Given the significant variability in the position of the heart in CT scans, such markers would provide the machine learning classifiers with a more meaningful description of the position of each component.

Example implementations of the coronary artery calcium scoring system and method will now be described with reference to FIGS. 7 to 13. The examples described are referred to as example method (and system) A, B and C.

Referring to FIG. 7, a test patient demographic table 120 is shown. In the examples, the same patients were used for methods B and C, and these patients were different to the patients used for method A.

The demographic information includes the number of patients 122 used in the training phase wherein machine learning aspects of the methods are trained, the age and age standard deviation of the patients used 124, the gender 126 of the patients used, and known calcium risk score data 128 indicative of how many test patients have a score of 0, 1-10, 11-100, 101-400 and greater than 400. In the examples, 1055 patients were used for the training phase for method A, 4807 patients were used for the training phase for methods B and C, 241 patients were used for testing method A and 1958 patients were used for testing methods B and C.

Figure 8:
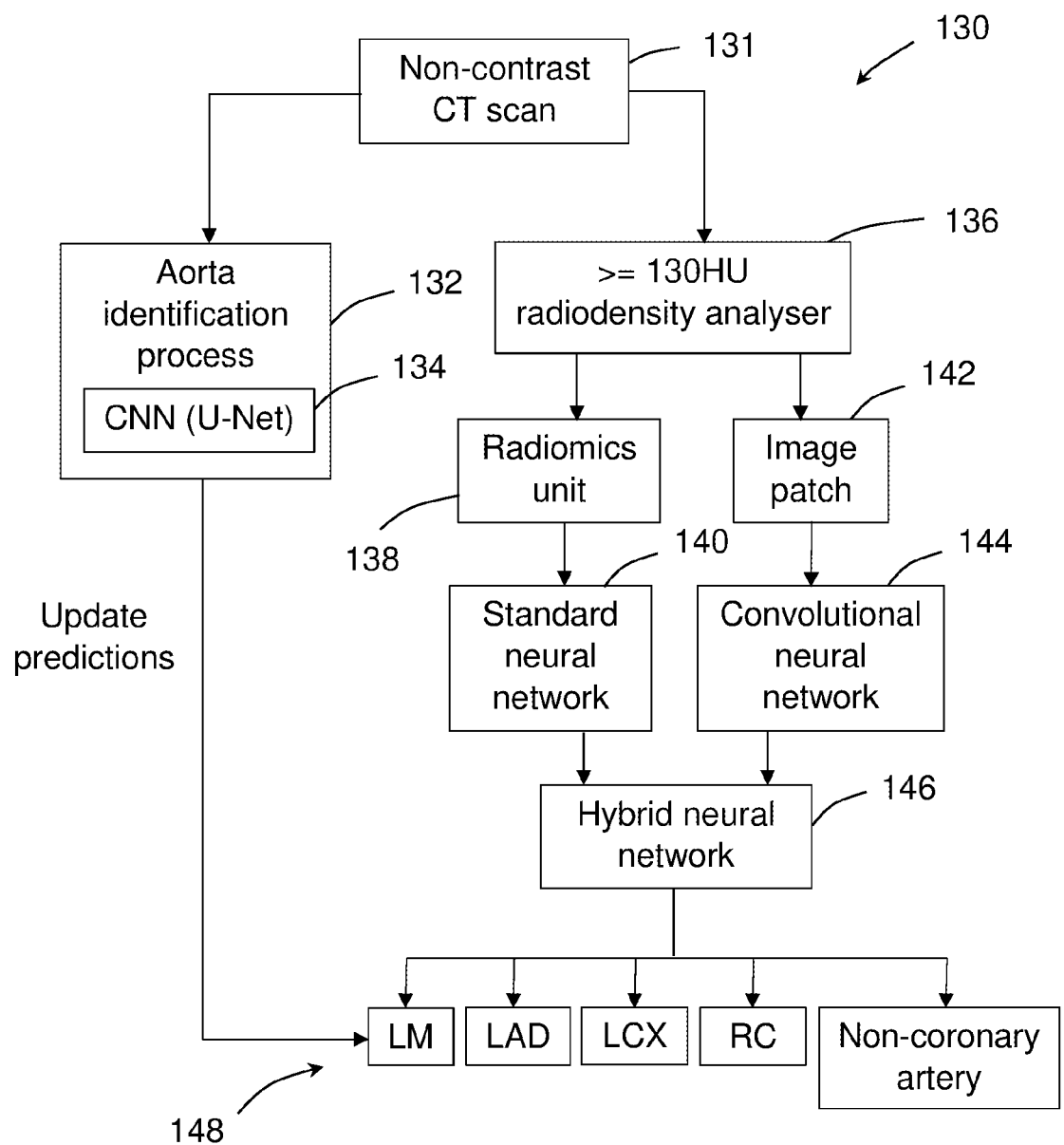
FIG. 8 is schematic block diagram of a first example system for calcium scoring of coronary arteries according to an embodiment of the invention.
Figure 9:
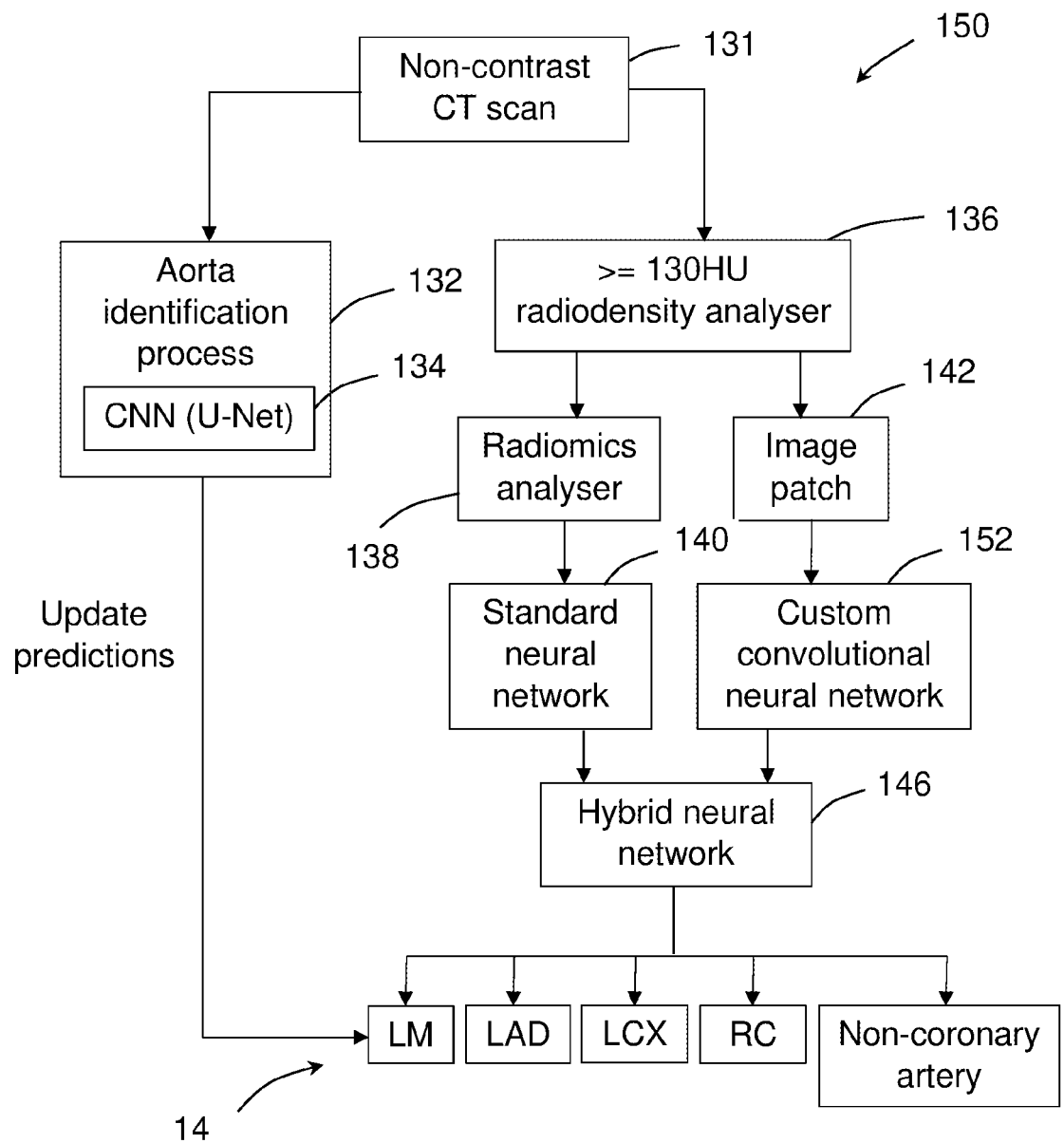
FIG. 9 is schematic block diagram of a second example system for calcium scoring of coronary arteries according to an embodiment of the invention.
Figure 10:
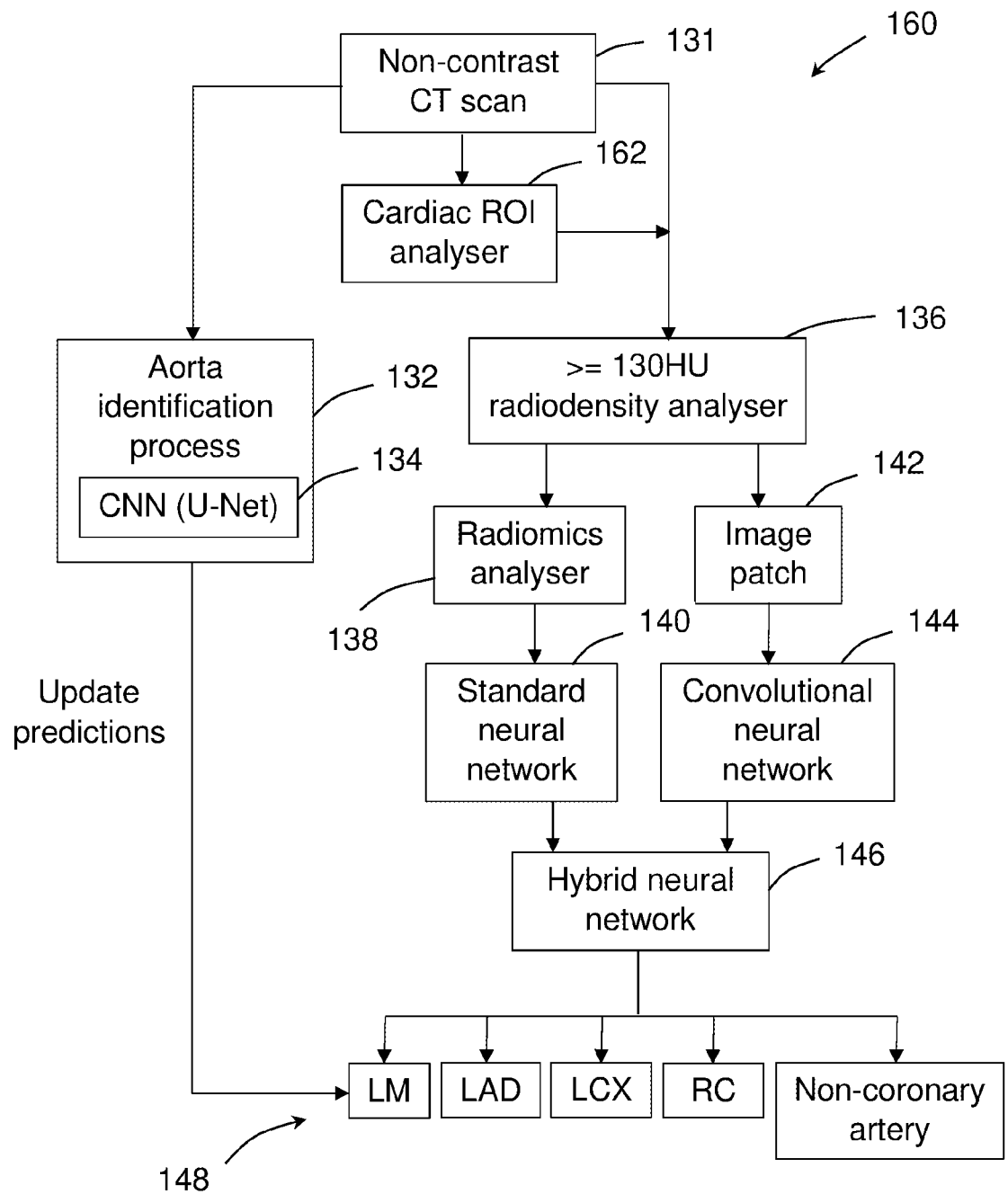
FIG. 10 is schematic block diagram of a third example system for calcium scoring of coronary arteries according to an embodiment of the invention.

Referring to FIGS. 8, 9 and 10, example systems A, B and C for implementing example methods A, B and C are shown.

As shown in FIG. 8, method and system A 130 is arranged to receive a non-contrast cardiac non-contrast CT data 131, and carry out an aorta identification process 132 on the received CT data using a U-Net convolutional neural network (CNN) 134 in order to segment ascending and descending portions of the aorta.

The system also passes the cardiac non-contrast CT data through a 130 Hounsfield Unit analyser 136, and the passed voxels are analysed by a radiomics unit 138 that generates candidate calcified volumes from the passed voxels and radiomic characteristic data for each candidate volume for analysis by a standard neural network 140 that is used instead of one or more classifiers to provide predictions for each candidate volume as to whether the volume is associated with a coronary artery. The passed voxels are also used with raw CT image data to generate an image patch 142 for each candidate volume, each image patch providing CT image context data for the region of the CT scan around the associated candidate volume. The image patches are analysed using a convolutional neural network 144 to provide predictions for each candidate volume as to whether the volume is associated with a coronary artery. In this example, the convolutional neural network is a standard AlexNet neural network arranged to analyse image patches in a 2D axial plane.

The predictions produced using the radiomic information and the image patches are input to a hybrid neural network 146 that uses the combined radiomic and image patch predictions to produce predictions for the candidate calcified volumes that are considered to be present on the coronary arteries, and predict the specific coronary arteries 148 on which calcified volumes are present.

The predictions are then updated, if necessary, by comparing with the aorta segmentation information and removing any calcified volumes that are actually present on the ascending or descending aorta, but have been misclassified as being present on a coronary artery.

Method and system B 150 shown in FIG. 9 is similar to method and system A 130 shown in FIG. 8 except that a custom convolutional neural network 152 is used to analyse the image patch information instead of the convolutional neural network 144. Like and similar features are indicated with like reference numerals. The custom convolutional neural network is arranged to analyse the region surrounding each image patches in multiple dimensions and in this way produces richer contextual information about the region surrounding each candidate calcified volume.

Method and system C 160 shown in FIG. 10 is similar to method and system B 140 shown in FIG. 9 except that a cardiac region of interest (ROI) analyser 162 is also provided to produce cardiac ROI information that is used to remove candidate calcified volumes that are present outside the region of interest around the heart, and therefore not present on a coronary artery. In this example, the ROI information is used to filter out regions of the received non-contrast CT scan before the Hounsfield Unit analysis is carried out. Like and similar features are indicated with like reference numerals.

Results of application of methods A, B and C indicate that method and system B provides better diagnostic accuracy and precision than method and system A, and method and system C provides better diagnostic accuracy and precision than method and system B.

Figures 11, 12:
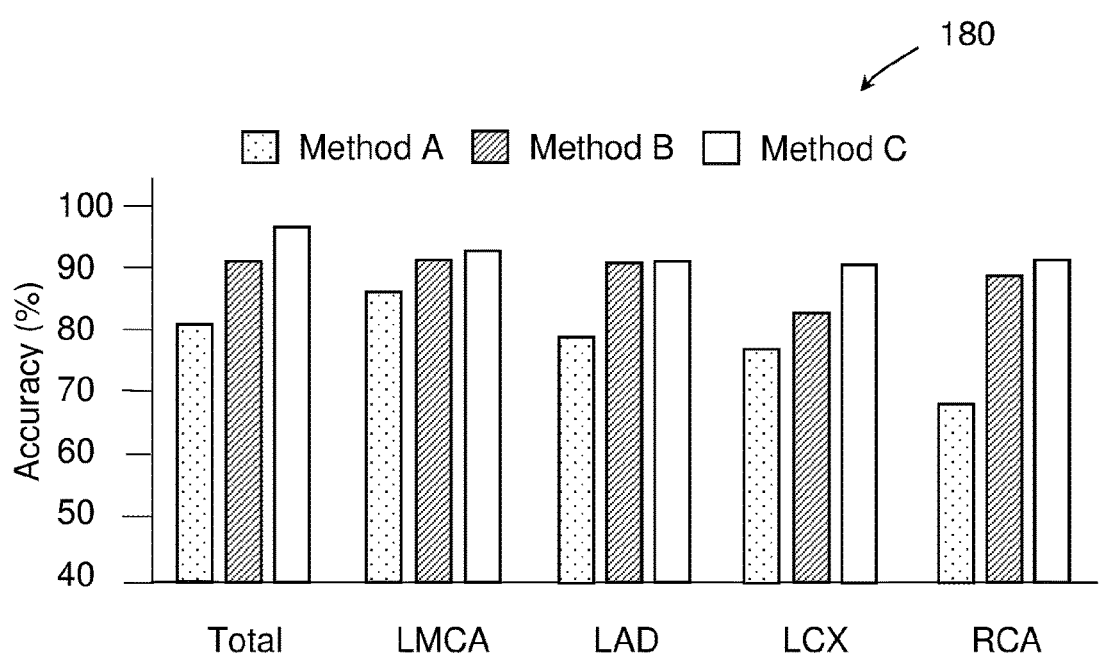
FIG. 11 is a calcium scoring results table associated with the system shown in FIG. 10.
FIG. 12 shows overall accuracy figures for the example systems shown in FIGS. 8, 9 and 10.

Application of method and system C to the test patient data referred to in FIG. 7 produced the results in method C results table 170 shown in FIG. 11.

The results table 170 shows results 172 of application of the present method and system C on a 1958 patient sample size, and results 174 of a conventional manually assisted CAC method on the same sample. The results indicate that method and system C accurately classifies 880 patients in calcium score risk category 0 (accuracy 99.44% compared to conventional manual assisted CAC), accurately classifies 233 patients in calcium score risk category 1-10 (accuracy 87.92%), accurately classifies 375 patients in calcium score risk category 11-100 (accuracy 96.15%), accurately classifies 267 patients in calcium score risk category 101-400 (accuracy 98.52%), and accurately classifies 142 patients in calcium score risk category >400 (accuracy 96.60%). The overall accuracy of method and system C is 96.88% compared to conventional manual assisted CAC.

Referring to FIG. 12, overall accuracy figures 180 for methods A, B and C are shown. It will be understood that the accuracy of method B is greater than method A, and the accuracy of method C is greater than method B.

Figure 13:
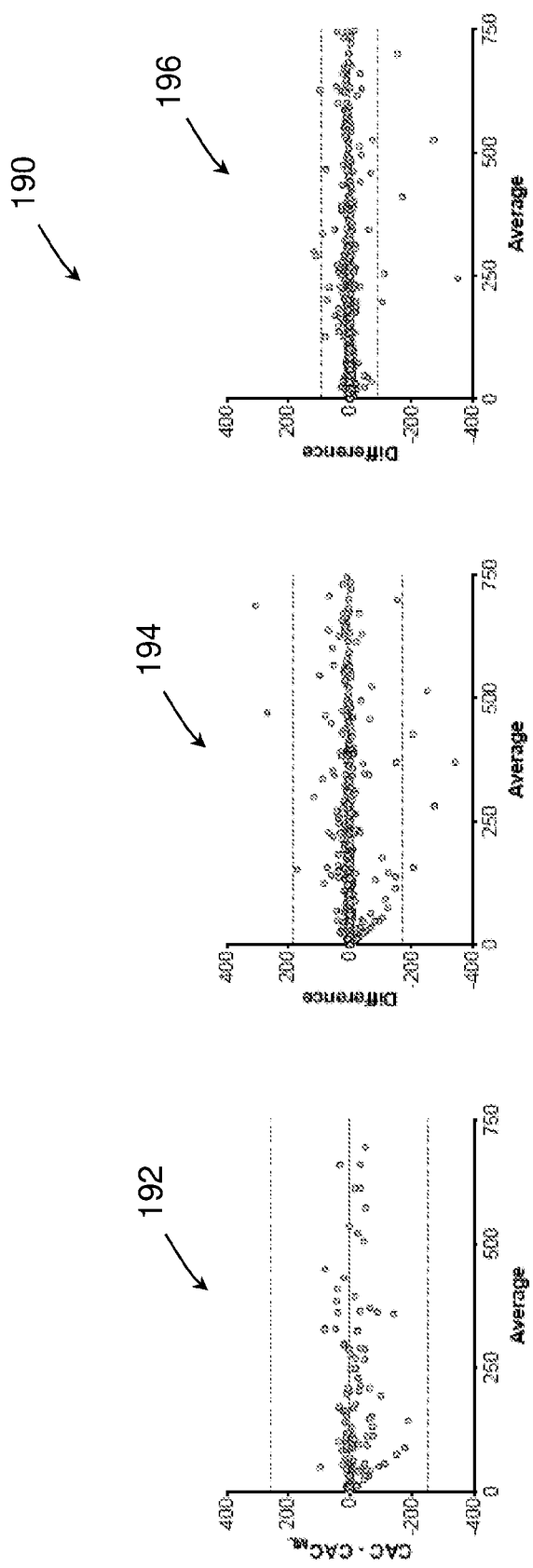
FIG. 13 shows overall precision figures for the example systems shown in FIGS. 8, 9 and 10.

Referring to FIG. 13, precision figures 190 for method A 192, method B 194 and method C 196 are shown, the precision figures including total precision, and precision for each coronary artery—the right coronary artery (RCA), the left main coronary (LMCA), the left anterior descending (LAD), and the left circumflex artery (LCX). It will be understood that the precision of method B is greater than method A, and the precision of method C is greater than method B.

While the above examples are described in relation to a method and system that is configured for identifying coronary artery calcifications and the particular coronary arteries in which the calcifications are located, it will be understood that the invention may also be applied to identification of calcifications on other anatomical structures of the heart. For example, the method and system may be used to locate and identify calcifications on the aorta.

With this arrangement, radiomic analysis is carried out to obtain a set of radiomic characteristics associated with the target anatomical component, such as the aorta or a portion of the aorta, and a misclassification remover used to avoid or remove misclassifications by carrying out segmentation of body components in a similar way to the examples described above. Like and similar features and method steps associated with the examples described above are applicable.

In the claims that follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

Modifications and variations as would be apparent to a skilled addressee are deemed to be within the scope of the present invention.

The invention claimed is:

1. A method of automatically determining a calcium score for at least one coronary component, the method comprising:
receiving cardiac non-contrast CT data indicative of a cardiac non-contrast CT scan carried out on a patient;
analysing the cardiac non-contrast CT data in a calcified components identifier to detect at least one candidate coronary calcified component associated with at least one target coronary anatomical structure;
analysing cardiac non-contrast CT data associated with the at least one candidate coronary calcified component using a radiomics analyser to determine radiomic characteristics of the at least one candidate coronary calcified component;
applying machine learning to the determined radiomic characteristics associated with each candidate coronary calcified component to identify any calcifications that are located on the at least one target coronary anatomical structure;
analysing the cardiac non-contrast CT data to identify at least one body component in the cardiac non-contrast CT data not associated with the at least one target coronary anatomical structure; and
after identifying any calcifications that are located on a coronary artery, using the identified at least one body component in the cardiac non-contrast CT data to remove misclassification of calcifications on the at least one coronary target anatomical structure that are located on the at least one identified body component.

2. The method as claimed in claim 1, wherein the at least one target coronary anatomical structure comprises at least one coronary artery.

3. The method as claimed in claim 2, comprising using machine learning to analyse the cardiac non-contrast CT data to identify at least one body component in the cardiac non-contrast CT data not associated with a coronary artery of the patient.

4. The method as claimed in claim 2, comprising:
analysing the cardiac non-contrast CT data to identify aortic components in the cardiac non-contrast CT data associated with an aorta of the patient; and
using the identified aortic components of the cardiac non-contrast CT data to remove misclassification of calcifications on a coronary artery that are located on the aortic components.

5. The method as claimed in claim 4, wherein the step of analysing the cardiac non-contrast CT data to identify aortic components of the cardiac non-contrast CT data associated with an aorta of the patient comprises analysing the identified aortic components using size, shape and position of the identified aortic components.

6. The method as claimed in claim 4, wherein the step of analysing the cardiac non-contrast CT data to identify aortic components in the cardiac non-contrast CT data associated with an aorta of the patient comprises:
progressively processing single slices of the cardiac non-contrast CT data, and assembling the results of a plurality of individual slices into a volumetric segmentation; and/or
processing volumetric inputs or cross-hair type orthogonal inputs.

7. The method as claimed in claim 2 comprising:
analysing the cardiac non-contrast CT data to identify a cardiac region of interest (ROI) around a heart in the cardiac non-contrast CT data; and
using the identified cardiac ROI to remove misclassification of calcifications on a coronary artery that are located outside the cardiac ROI.

8. The method as claimed in claim 2, wherein the determined radiomic characteristics include position, shape, size and/or density.

9. The method as claimed in claim 2, comprising using a first classifier to classify each candidate coronary artery calcified component as located on a coronary artery or not located on a coronary artery, and a second classifier to identify each coronary artery.

10. The method as claimed in claim 2, comprising analysing the cardiac non-contrast CT data indicative of the candidate coronary artery calcified components to determine image patch data associated with a region of the cardiac non-contrast CT data around each candidate coronary artery calcified component, and applying machine learning to the determined image patch data to identify any calcifications that are located on a coronary artery.

11. The method as claimed in claim 10, comprising using a hybrid neural network to combine the output of the step of applying machine learning to the determined image patch data to identify any calcifications that are located on a coronary artery using a convolutional neural network, and the determined radiomic characteristics associated with each candidate coronary artery calcified component.

12. The method as claimed in claim 2, comprising directly applying machine learning to the cardiac non-contrast CT data indicative of the candidate coronary artery calcified components to identify any calcifications that are located on a coronary artery.

13. The method as claimed in claim 12, comprising using outputs of the directly applied machine learning and outputs of the step of applying machine learning to the determined radiomic characteristics to identify any calcifications that are located on a coronary artery.

14. The method as claimed in claim 2, comprising:
analysing the cardiac non-contrast CT data to identify a mitral valve in the cardiac non-contrast CT data, and using the identified mitral valve to remove misclassification of calcifications; and/or
analysing the cardiac non-contrast CT data to identify a heart in the cardiac non-contrast CT data, and using the identified heart to remove misclassification of calcifications on a coronary artery that are located outside the heart.

15. The method as claimed in claim 2, comprising adding calibration markers manually to the cardiac non-contrast CT data and using the added markers to provide the machine learning with positional information.

16. A system for automatically determining a calcium score for at least one coronary component, the system comprising:
a calcified components identifier for analysing received cardiac non-contrast CT data indicative of a cardiac non-contrast CT scan carried out on a patient to detect at least one candidate coronary calcified component associated with at least one target coronary anatomical structure;
a radiomics analyser for analysing cardiac non-contrast CT data associated with the at least one candidate coronary calcified component to determine radiomic characteristics of the at least one candidate coronary calcified component;
a radiomic machine learning component arranged to apply machine learning to the determined radiomic characteristics associated with each candidate coronary calcified component to identify any calcifications that are located on the at least one target coronary anatomical structure;
a body component identifier arranged to analyse the cardiac non-contrast CT data after any calcifications have been located on a coronary artery to identify at least one body component in the cardiac non-contrast CT data not associated with the at least one target coronary anatomical structure; and
a misclassification remover that uses the identified at least one body component in the cardiac non-contrast CT data to remove misclassification of calcifications on the at least one coronary target anatomical structure that are located on the at least one identified body component.

17. The system as claimed in claim 16, wherein the at least one target coronary anatomical structure comprises at least one coronary artery.

18. The system as claimed in claim 17, wherein the body component analyser uses machine learning to analyse the cardiac non-contrast CT data to identify at least one body component in the cardiac non-contrast CT data not associated with a coronary artery of the patient.

19. The system as claimed in claim 17, comprising:
an aorta identifier for analysing the cardiac non-contrast CT data to identify aortic components in the cardiac non-contrast CT data associated with an aorta of the patient;
the system using the identified aortic components of the cardiac non-contrast CT data to remove misclassification of calcifications on a coronary artery that are located on the aortic components.

20. The system as claimed in claim 17, comprising:
a cardiac region of interest (ROI) identifier for analysing the cardiac non-contrast CT data to identify a cardiac region of interest (ROI) around a heart in the cardiac non-contrast CT data; and
the system using the identified cardiac ROI used to remove misclassification of calcifications on a coronary artery that are located outside the cardiac ROI.

21. The system as claimed in claim 17, wherein the determined radiomic characteristics include position, shape, size and/or density.

22. The system as claimed in claim 17, wherein the calcified components identifier comprises an image patch analyser arranged to analyse the cardiac non-contrast CT data indicative of the candidate coronary artery calcified components to determine image patch data associated with a region of the cardiac non-contrast CT data around each candidate coronary artery calcified component, and apply machine learning to the determined image patch data to identify any calcifications that are located on a coronary artery.

23. The system as claimed in claim 22, comprising a hybrid neural network for combining an output of the image patch convolutional neural network with an output of the radiomic machine learning component.

24. A method of automatically determining a calcium score for at least one coronary artery, the method comprising:

receiving cardiac non-contrast CT data indicative of a cardiac non-contrast CT scan carried out on a patient;

analysing the cardiac non-contrast CT data in a calcified components identifier using machine learning to identify candidate calcifications located on the at least one coronary artery;

analysing the cardiac non-contrast CT data to identify aortic components in the cardiac non-contrast CT data associated with an aorta of the patient; and using the identified aortic components in the cardiac non-contrast CT data to remove misclassification of calcifications on the at least one coronary artery that are located on the aortic components.

25. The method as claimed in claim 24, wherein the method comprises analysing the cardiac non-contrast CT data to identify ascending and descending portions of the aorta.

26. The method as claimed in claim 25, comprising using machine learning to predict whether each voxel of the cardiac non-contrast CT data is part of the ascending or descending aorta and produce candidate aorta voxels.

27. The method as claimed in claim 26, comprising applying a connected component analysis to the candidate aorta voxels to identify neighbouring voxels that belong to the same aortic component.

* * * * *